US00PP20449P2

(12) United States Plant Patent
Caster et al.

(10) Patent No.: US PP20,449 P2
(45) Date of Patent: Nov. 3, 2009

(54) BLUEBERRY PLANT NAMED 'DRISBLUEONE'

(50) Latin Name: *Vaccinium corymbosum*
Varietal Denomination: DrisBlueOne

(75) Inventors: Brian Caster, Watsonville, CA (US); Arlen Draper, Payson, AZ (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 12/082,278

(22) Filed: Apr. 10, 2008

(51) Int. Cl.
*A01H 5/00* (2006.01)

(52) U.S. Cl. ..... Plt./157

(58) Field of Classification Search ..... Plt./157
See application file for complete search history.

*Primary Examiner*—June Hwu
(74) *Attorney, Agent, or Firm*—Jondle & Associates, P.C.

(57) ABSTRACT

This invention relates to a new and distinct cultivar of blueberry plant named 'DrisBlueOne' primarily characterized by large berries with medium sweetness, medium acidity, and slightly oblate spherical berry shape and berries that have green flesh, is disclosed.

2 Drawing Sheets

Genus and species: *Vaccinium corymbosum.*
Variety denomination: 'DrisBlueOne'.

BACKGROUND OF THE NEW PLANT

The present invention relates to a new and distinct blueberry cultivar designated 'DrisBlueOne' and botanically known as *Vaccinium corymbosum*. This new blueberry cultivar was discovered in Watsonville, Santa Cruz County, Calif. in September 2000 as a result of a hybridization between the female parent, 'MS7' a proprietary unpatented variety and the male parent, 'Jubilee' an unpatented variety.

The original seedling of the new cultivar was asexually propagated at a nursery in Watsonville, Monterey County, Calif. 'DrisBlueOne' was subsequently asexually propagated and underwent further testing at a nursery in Watsonville, Santa Cruz County, Calif. for seven years. 'DrisBlueOne' has been asexually propagated via softwood cuttings. The present invention has been found to be stable and reproduce true to type through successive asexual propagations.

SUMMARY OF THE INVENTION

The following are the most outstanding and distinguishing characteristics of this new cultivar when grown under normal horticultural practices in Watsonville, Santa Cruz County, Calif.

1. Large berries with medium sweetness;
2. Medium acidity and a slightly oblate spherical berry shape; and
3. Berries that have green flesh.

DESCRIPTION OF THE PHOTOGRAPHS

The accompanying color photographs show typical specimens of the new cultivar at various stages of development as nearly true as it is possible to make in color reproductions. The photographs are of plants that are 7 years old.

DESCRIPTION OF THE NEW CULTIVAR

Figure 1:
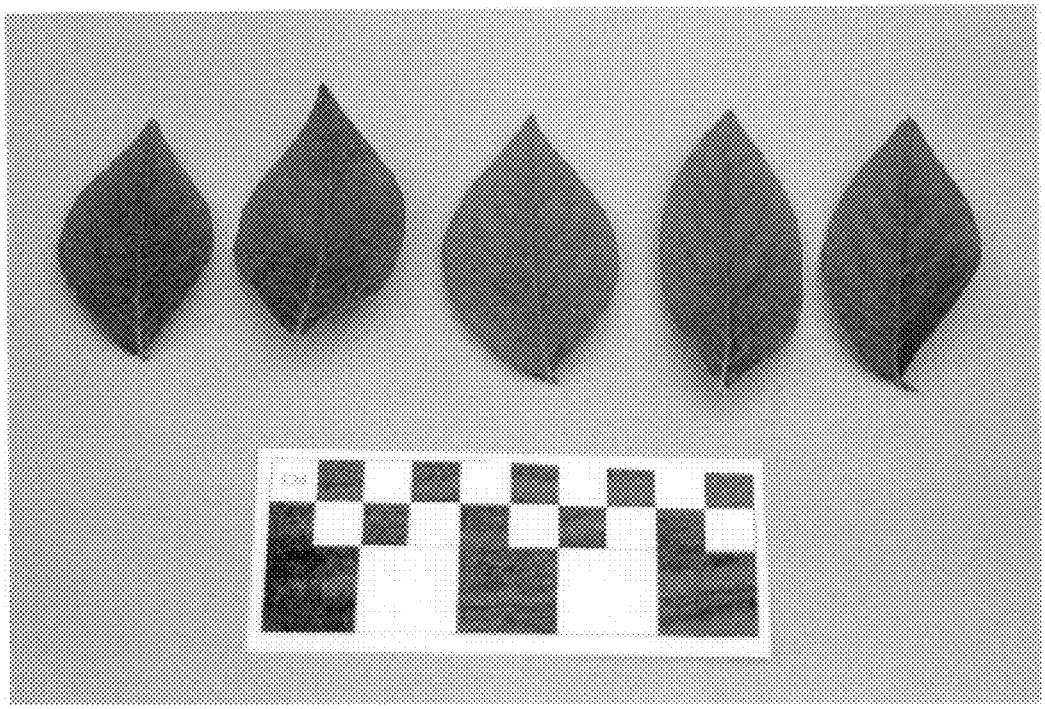
FIG. 1 shows both the upper surface and lower surface of the leaves.
Figure 2:
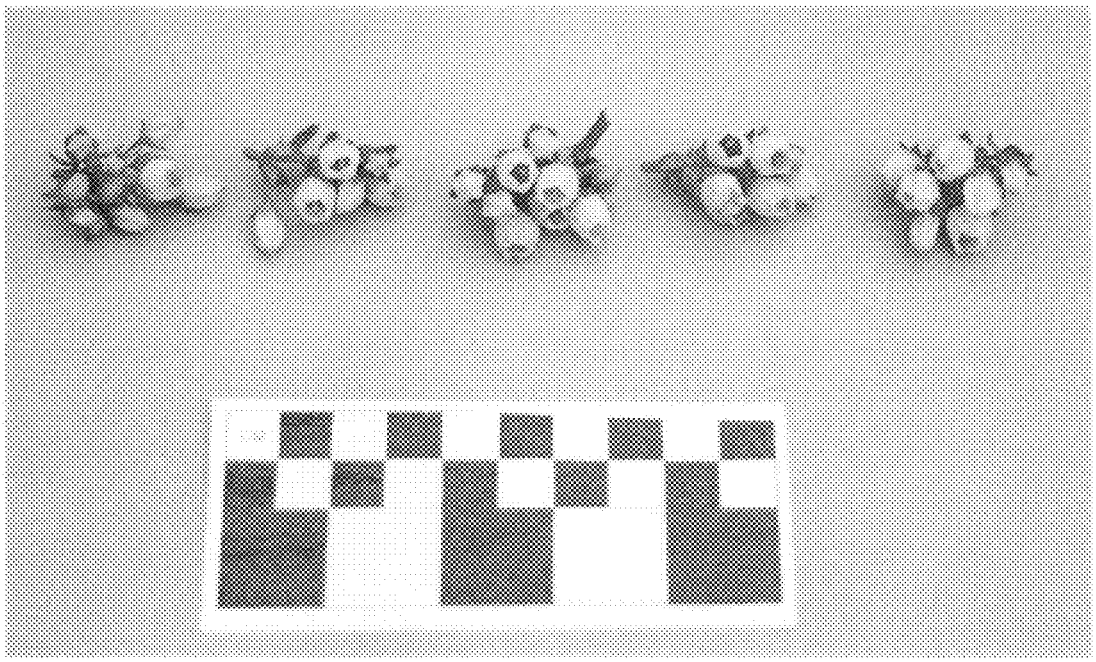
FIG. 2 shows the mature flowers.
Figure 3:
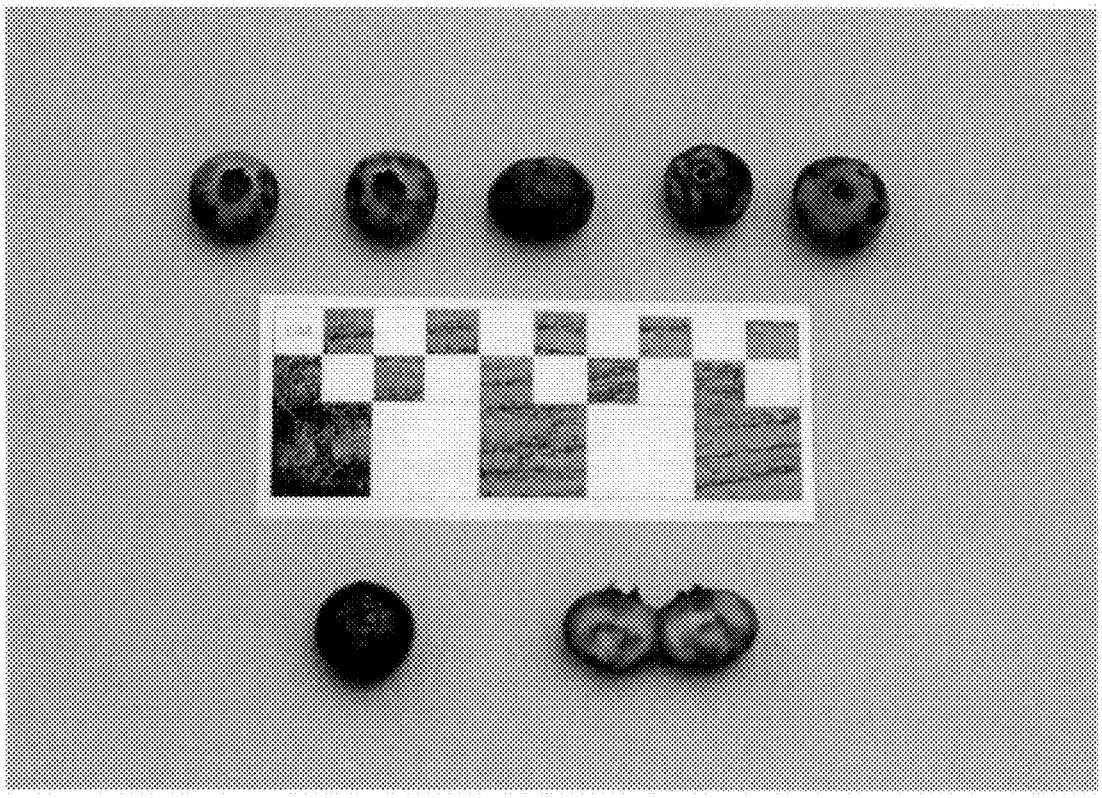
FIG. 3 shows the whole fruit and a longitudinal-section of the fruit.

The following description of 'DrisBlueOne' is based on observations taken from the 2007 growing season in Watsonville, Santa Cruz County, Calif., where the age of the 'DrisBlueOne' plants was 7 years, while the age of the comparison variety 'O'Neal' plants was 12 years old. All descriptions are in accordance with UPOV terminology. Color designations, color descriptions, and other phenotypical descriptions may deviate from the stated values and descriptions depending upon variation in environmental, seasonal, climatic and cultural conditions. 'DrisBlueOne' has not been observed under all possible environmental conditions. Color terminology follows The Royal Horticultural Society Colour Chart, London (R.H.S.) (2001).

DETAILED BOTANICAL DESCRIPTION

Table 1 shows plant characteristics of the new variety compared with plant characteristics of blueberry plant 'O'Neal' (unpatented). Table 1 includes plant, canopy and cane characteristics.

TABLE I

| Characteristic | 'DrisBlueOne' | 'O'Neal' |
|---|---|---|
| Plant: | | |
| Vigor | Strong | Low |
| Growth habit | Bushy | Bushy |
| Chilling requirement | Medium | Medium |
| Propagation | From softwood cuttings | From softwood cuttings |
| Canopy: | | |
| Bush height (cm) | 55 | 134 |
| Canopy width (cm) | 63 | 124 |
| Height/Width ratio | 0.9 | 1.1 |

TABLE I-continued

| Characteristic | 'DrisBlueOne' | 'O'Neal' |
|---|---|---|
| Canes: | | |
| Age at maturity (years) | 3 years | 3 years |
| Mature cane texture | Rough | Rough |
| Mature cane diameter (cm) | 1.08 | 0.734 |
| Mature cane length (cm) | 66.2 | 69.0 |
| Mature cane color | RHS 146C (yellow-green) | RHS 138A (green) |
| Cane renewal | Medium | Weak |

Table 2 shows plant characteristics of the new variety compared with plant characteristics of blueberry plant 'O'Neal' (unpatented). Table 2 includes bud, calyx, corolla, flower and pedicel characteristics. Where "n/a" appears for a characteristic, it indicates a characteristic is not available.

TABLE 2

| Characteristic | 'DrisBlueOne' | 'O'Neal' |
|---|---|---|
| Bud: | | |
| Time of bud break | Medium | Early |
| Flowers per bud | 10 | 6 |
| Calyx: | | |
| Diameter at anthesis (cm) | 0.856 | 0.658 |
| Lobe count | 5 | 5 |
| Color | RHS 139A (dark green) | RHS 145C (light yellow-green) |
| Corolla: | | |
| General | Petals fused into a corolla with 5 lobes | Petals fused into a corolla with 5 lobes |
| Length (cm) | 0.794 | 1.014 |
| Diameter (cm) | 0.838 | 0.886 |
| Aperature diameter (cm) | 0.58 | 0.334 |
| Mature color | RHS 157C (green-white) | RHS 155A (white) |
| Flower: | | |
| Type | Perfect hypogynous (inferior ovary); stamens attached at base of fused corolla tube | Perfect hypogynous (inferior ovary); stamens attached at base of fused corolla tube |
| Shape | Urceolate | Urceolate |
| Fragrance | Faint | Very faint |
| Size | Large | Medium |
| 50% anthesis (full bloom) | March 18$^{th}$ | n/a |
| 1% bloom | Medium | Early |
| Pedicel: | | |
| Color | RHS 143D (green-white) | RHS 144D (light yellow-green) |
| Length (cm) | 0.678 | 0.478 |

Table 3 shows plant characteristics of the new variety compared with plant characteristics of blueberry plant 'O'Neal' (unpatented). Table 3 includes leaf and shoot characteristics.

TABLE 3

| Characteristic | 'DrisBlueOne' | 'O'Neal' |
|---|---|---|
| Leaves: | | |
| Arrangement | Alternate | Alternate |
| Shape | Broadly elliptic to oval | Simple and broadly elliptic to slightly ovate |
| Apex | Broadly acute | Broadly acute |

TABLE 3-continued

| Characteristic | 'DrisBlueOne' | 'O'Neal' |
|---|---|---|
| Base | Broadly acute to rounded | Broadly acute to slightly cuneate |
| Margin | Entire | Entire |
| Pubescence (both surfaces) | Glabrous | Glabrous |
| Length (cm) | 6.502 | 6.620 |
| Width (cm) | 3.958 | 3.440 |
| Length/width ratio | 1.6 | 1.9 |
| Color, upper surface | RHS 137A (green) | RHS 137A (green) |
| Color, lower surface | RHS 137C (green) | RHS 138B (green) |
| Venation | Reticulate | Reticulate |
| Petiole: | | |
| Length (cm) | 0.37 | 0.40 |
| Color | RHS 145B (yellow-green) | RHS N144D (yellow-green) |
| Shoots: | | |
| Internode length (cm) | 1.72 | 1.634 |

Table 4 shows plant characteristics of the new variety compared with plant characteristics of blueberry plant 'O'Neal' (unpatented). Table 4 includes berry, skin, peduncle and seed characteristics.

TABLE 4

| Characteristic | 'DrisBlueOne' | 'O'Neal' |
|---|---|---|
| Berry: | | |
| Shape | Slightly oblate sphere | Slightly oblate sphere |
| Size | Large | Medium |
| Weight (g) | 1.77 | 1.39 |
| Height (cm, pedicel scar to calyx) | 1.346 | 1.284 |
| Diameter (cm at widest point) | 1.684 | 1.508 |
| Height/diameter ratio | 0.80 | 0.85 |
| Firmness | Very firm | Medium |
| Sweetness | Medium | Strong |
| Acidity | Medium | Mild |
| Season/timing (25% ripe) | Mid-season | Early season |
| Season/timing (50% ripe) | June 17$^{th}$ | June 14$^{th}$ |
| Pedicel scar diameter (cm) | 0.248 | 0.16 |
| Skin: | | |
| Bloom deposition | Strong/heavy | Medium |
| Mature color with bloom | RHS 104D (blue) | RHS 98C (violet-blue) |
| Mature color without bloom | RHS 103A (blue) | RHS 103A (blue) |
| Immature color with bloom | RHS 142C (green) | RHS 143D (light green) |
| Flesh: | | |
| Color | RHS 145B (green) | RHS 157A (green-white) |
| Seed: | | |
| Abundance | 16 per fruit | 27 per fruit |
| Color | RHS N167A (orange-brown) | RHS 165B (greyed-orange) |
| Length (cm) | 0.184 | 0.200 |
| Width (cm) | 0.124 | 0.112 |
| Length/width ratio | 1.48 | 1.79 |

Table 5 shows plant characteristics of the new variety compared with plant characteristics of blueberry plant 'O'Neal' (unpatented). Table 5 includes the reproductive organs.

TABLE 5

| Characteristic | 'DrisBlueOne' | 'O'Neal' |
|---|---|---|
| Reproductive Organs: | | |
| Ovary color | RHS 122A (blue-green) | RHS 133C (green) |
| Pollen color | RHS 11C (yellow) | RHS 8D (light yellow) |
| Anther color | RHS 172B (greyed-orange) | RHS N170A (greyed-orange) |
| Style length, including stigma (cm) | 0.812 cm | 0.810 cm |
| Pollination requirement | Believed to be self-fertile | |

Resistance to diseases and insects: Disease and insect resistance are typical of the species.

COMPARISON WITH PARENTAL VARIETIES

When 'DrisBlueOne' is compared to the female parent 'MS7' (unpatented), 'DrisBlueOne' has a more spherical berry shape and stronger flavor, while 'MS7' has a more oblate berry shape and a milder flavor.

When 'DrisBlueOne' is compared to the male parent 'Jubilee' (unpatented), 'DrisBlueOne' has a bushy growth habit and large berries, while 'Jubilee' has an upright growth habit and small to medium-sized berries.

We claim:

1. A new and distinct cultivar of blueberry plant as described and shown herein.

* * * * *